United States Patent
Mobasser et al.

(10) Patent No.: US 9,387,026 B2
(45) Date of Patent: Jul. 12, 2016

(54) BONE FASTENER AND METHODS OF USE

(71) Applicant: Warsaw Orthopedic, Inc., Warsaw, IN (US)

(72) Inventors: Jean-Pierre Mobasser Mobasser, Indianapolis, IN (US); Y. Raja Rampersaud, Toronto (CA); Joshua W. Simpson, Collierville, TN (US); Nicholas Benson, Cordova, TN (US); William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 448 days.

(21) Appl. No.: 13/827,096

(22) Filed: Mar. 14, 2013

(65) Prior Publication Data

US 2014/0277193 A1 Sep. 18, 2014

(51) Int. Cl.
*A61B 17/86* (2006.01)
*A61B 17/70* (2006.01)

(52) U.S. Cl.
CPC ......... *A61B 17/8625* (2013.01); *A61B 17/7037* (2013.01)

(58) Field of Classification Search
CPC ............... A61B 17/58; A61B 17/7001; A61B 17/7058; A61B 17/7005; A61B 17/7032; A61B 17/7034; A61B 17/7035; A61B 17/86; A61B 17/863; A61B 17/8635; A61B 2017/8675
USPC ............................................... 81/54, 463, 464
See application file for complete search history.

(56) References Cited

U.S. PATENT DOCUMENTS

| | | | |
|---|---|---|---|
| 7,044,953 B2 * | 5/2006 | Capanni | 606/309 |
| 7,798,757 B2 * | 9/2010 | Kawano et al. | 411/408 |
| 7,802,500 B2 * | 9/2010 | Kolodziej et al. | 81/434 |
| 8,568,317 B1 * | 10/2013 | Gharib et al. | 600/437 |

* cited by examiner

*Primary Examiner* — Anu Ramana

(57) ABSTRACT

A bone fastener comprises a first end and a second end defining a longitudinal axis and being configured to penetrate tissue. The second end has a first portion having a thread diameter and a core diameter. The second portion has a core diameter less than the core diameter of the first portion. The second portion includes a threaded surface and a substantially even surface. Systems and methods are disclosed.

20 Claims, 3 Drawing Sheets

BONE FASTENER AND METHODS OF USE

TECHNICAL FIELD

The present disclosure generally relates to medical devices for the treatment of spinal disorders, and more particularly to a spinal implant system including a bone fastener that provides stabilization while reducing stress on spinal elements.

BACKGROUND

Spinal disorders such as degenerative disc disease, disc herniation, osteoporosis, spondylolisthesis, stenosis, scoliosis and other curvature abnormalities, kyphosis, fracture and instability may result from factors including congenital or developmental abnormalities, trauma, infection, tumor, metabolic and inflammatory diseases and degenerative conditions related to aging. Spinal disorders typically result in symptoms including pain, nerve damage (loss of feeling and or weakness), and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion, realignment, deformity correction and implantable prosthetics. During surgical treatment, one or more rods may be attached via fasteners to the exterior of two or more vertebral members to provide stability to a treated region. This disclosure describes an improvement over these prior art technologies.

SUMMARY

Accordingly, a spinal implant system is provided. In one embodiment, in accordance with the principles of the present disclosure, the spinal implant system includes a bone fastener. The bone fastener comprises a first end and a second end defining a longitudinal axis and being configured to penetrate tissue. The second end has a first portion having a thread diameter and a core diameter and a second portion. The second portion has a core diameter less than the core diameter of the first portion. The second portion includes a threaded surface and a substantially even surface.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
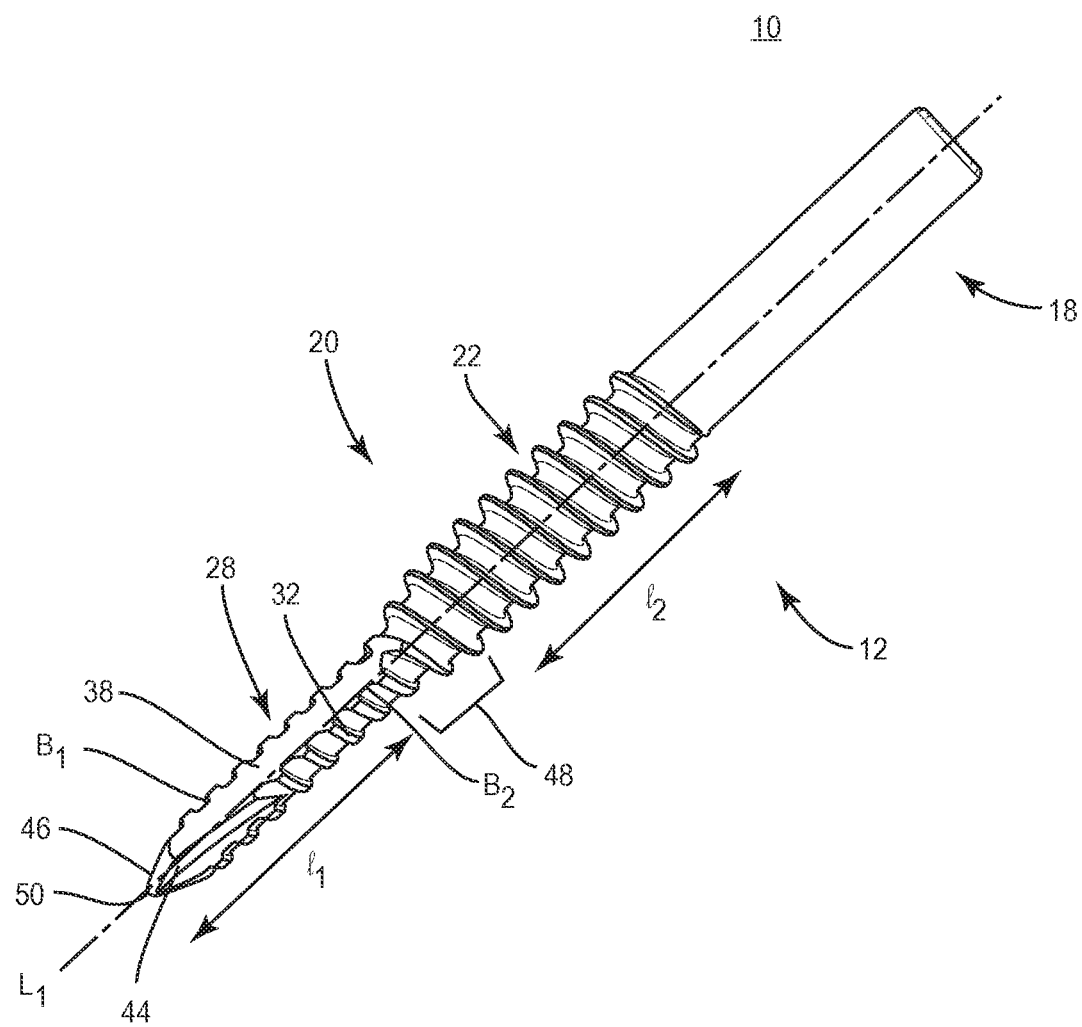
FIG. 1 is a perspective view of a component of one embodiment of a system in accordance with the principles of the present disclosure.

The exemplary embodiments of a surgical system and methods of use disclosed are discussed in terms of medical devices for the treatment of spinal disorders and more particularly, in terms of a spinal implant system including a bone fastener that provides stabilization while reducing stress on spinal elements, In one embodiment, the system includes a bone fastener comprising a probe having a shallow thread form disposed therealong. This configuration facilitates drawing and/or pulling the fastener into tissue, such as, for example, bone.

In one embodiment, the system includes a bone fastener having a distal end, which includes a distal portion and a threaded proximal portion. The distal portion is a probe having an outside diameter that is smaller than a core diameter of the threaded proximal portion to provide adequate bone fastener interface strength. In one embodiment, the bone fastener has a threaded probe at its distal portion having a thread depth that is shallower than the thread depth of the proximal portion of the bone fastener. In one embodiment, the proximal portion includes a cortical thread. In one embodiment, the probe has a shallow thread form that facilitates drawing the bone fastener into bone. In one embodiment, the bone fastener includes an increase in the length of the helix thread form in contact with bone.

In one embodiment, the probe includes a substantially even surface, such as, for example, a length of flats that range from 15-20 millimeters (mm) at its distal portion to allow the bone fastener to be probed or inserted through a pedicle into a vertebral body. The probe tip can be inserted by either threading the tip into bone or by an oscillation type of motion. In one embodiment, a distal tip of the probe has approximately 10 mm radial cutting flutes. This configuration provides visual indicia, for example, to allow a surgeon to redirect the bone fastener within bone.

In one embodiment, the system includes a transition disposed between the distal portion and the proximal portion of the distal end of the bone fastener. In one embodiment, the transition is disposed in a range of approximately 10 to 30 degrees relative to a longitudinal axis of the bone fastener. In one embodiment, the transition is disposed at approximately 15 degrees relative to a longitudinal axis of the bone fastener. This configuration provides a smooth starting of cortical threads as well as requiring a lower axial force to engage the threads. In one embodiment, the bone fastener provides an effective deeper thread at the transition area, which is approximately 20 mm from the distal tip of the bone fastener.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteo and bone related applications, including those associated with diagnostics and therapeutics. In some embodiments, the disclosed system and method may be alternatively employed in a surgical treatment with a patient in a prone, lateral or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and method of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
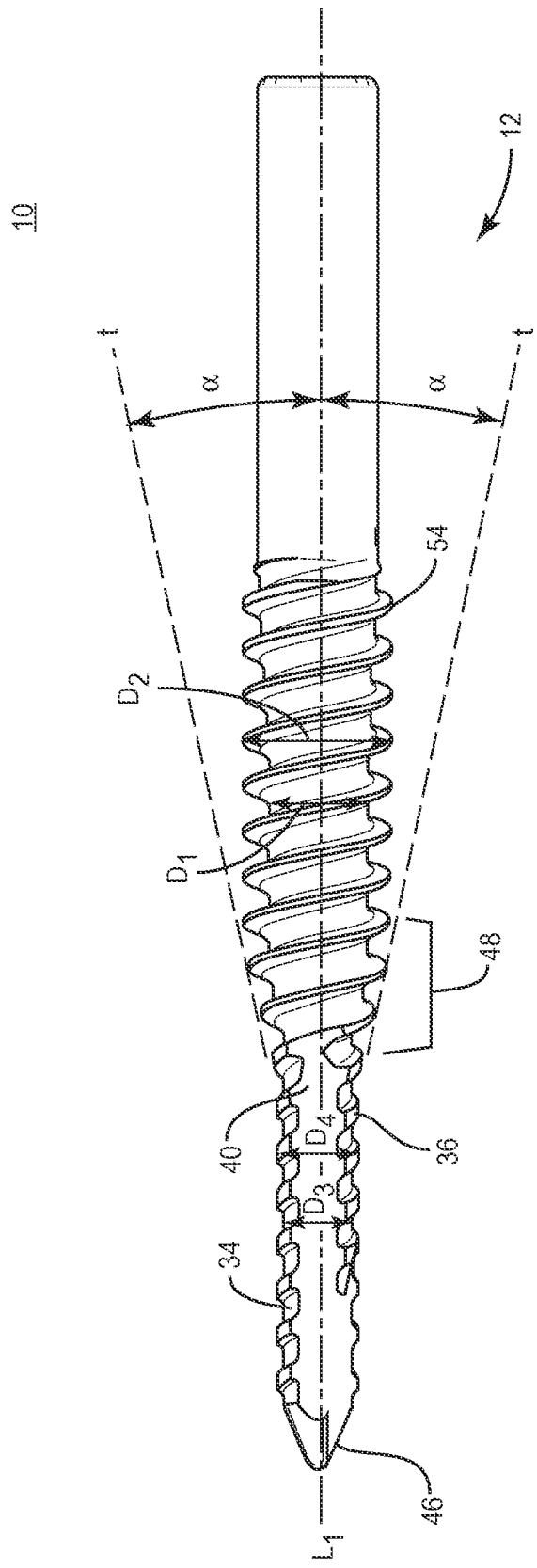
FIG. 2 is a side view of the component shown in FIG. 1.

The following discussion includes a description of a spinal implant system including a bone fastener, related components and exemplary methods of employing the bone fastener in accordance with the principles of the present disclosure. Alternate embodiments are also disclosed. Reference will now be made in detail to the exemplary embodiments of the present disclosure, which are illustrated in the accompanying figures. Turning now to FIGS. 1-2, there are illustrated components of a spinal implant system including a bone fastener 10 in accordance with the principles of the present disclosure.

The components of the spinal implant system can be fabricated from biologically acceptable materials suitable for medical applications, including metals, synthetic polymers, ceramics and bone material and/or their composites, depending on the particular application and/or preference of a medical practitioner. For example, the components of the spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the spinal implant system, individually or collectively, may also be fabricated from a heterogeneous material such as a combination of two or more of the above-described materials. The components of the spinal implant system may be monolithically formed, integrally connected or include fastening elements and/or instruments, as described herein.

Bone fastener 10 comprises, such as, for example, a shaft 12 having a circular cross section configuration that extends between a first end, such as, for example, a proximal end 18 and a second end, such as for example, a distal end 20. Shaft 12 has a substantially cylindrical cross section and defines a longitudinal axis L1. In some embodiments, shaft 12 may have alternate cross section configurations, such as, for example, oval, oblong, triangular, square, polygonal, irregular, uniform, non-uniform, offset, staggered, undulating, arcuate, variable and/or tapered.

In some embodiments, the outer surface of shaft 12 may include one or a plurality of openings. It is contemplated that all or only a portion of the outer surface of shaft 12 may have alternate surface configurations to enhance fixation with tissue such as, for example, rough, arcuate, undulating, mesh, porous, semi-porous, dimpled and/or textured according to the requirements of a particular application. In some embodiments, all or only a portion of shaft 12 may be disposed at alternate orientations, relative to axis L1, such as, for example, transverse, perpendicular and/or other angular orientations such as acute or obtuse, co-axial and/or may be offset or staggered. In some embodiments, all or only a portion of shaft 12 may be cannulated.

Distal end 20 is configured for penetration and fixation with vertebral tissue. Distal end 20 has a first portion, such as, for example, a proximally threaded portion 22 configured to engage tissue, such as, for example, a vertebra pedicle. Proximally threaded portion 22 has a cylindrical cross section configuration and includes an outer surface having an external thread 54. Proximally threaded portion 22 includes dimensions, such as, for example, a core diameter D1, a minor thread diameter and a maximum thread diameter D2 Proximally threaded portion 22 includes a length l2.

Thread 54 has a substantially triangular thread form and is configured to penetrate bone. In one embodiment, portion 22 is configured for engagement and fixation with cortical bone such that its threads are more closely spaced and have a shallow cutting configuration. In one embodiment, portion 22 is configured for engagement and fixation with cancellous bone such that its threads have a deeper cutting configuration and are more widely spaced apart. In some embodiments, portion 22 can include cortical thread and cancellous thread portions, or a lag configuration. In some embodiments, the thread form can be variously configured, such as, for example, V-shaped, buttress, isosceles, scalene, equilateral, truncated, square and/or trapezoidal. In some embodiments, thread 54 can be coarse, fine and/or configured for engagement with a selected portion of vertebral tissue, such as, for example, cortical and cancellous bone.

In some embodiments, thread 54 may include a single thread turn or a plurality of discrete threads. In some embodiments, other engaging structures may be located on proximally threaded portion 22, such as, for example, a nail configuration, barbs, expanding elements, raised elements and/or spikes to facilitate engagement of proximally threaded portion 22 with tissue, such as, for example, vertebrae.

Bone fastener 10 has a transition portion 48 extending distally from proximally threaded portion 22. Transition portion 48 is disposed between proximally threaded portion 22 and a second portion of distal end 20, such as, for example, a probe 28 described below. Transition portion 48 is tapered from diameter D2 of portion 22 to a dimension, such as, for example, a smaller diameter D4, described below, of probe 28, and diameter D1 of portion 22 to a dimension, such as, for example, a smaller diameter D3 of probe 28.

The tapered configuration of transition portion 48 defines tapered axes t that are disposed at an angular orientation a relative to longitudinal axis L1 In some embodiments, angular orientation a includes a range of approximately 10 through 30 degrees. In one embodiment, angular orientation a includes an angular orientation of substantially 15 degrees relative to longitudinal axis L1.

Probe 28 extends distally from portion 22 and directly from portion 48, and is configured to engage tissue, such as, for example, vertebrae. Probe 28 has a circumscribed cylindrical cross section configuration and includes an outer surface having an external thread 32. Probe 28 includes a core diameter D3, a minor thread diameter and a maximum thread diameter D4. Diameter D4 has a dimension less than core diameter D1 of proximally threaded portion 22. Diameter D3 has a dimension less than diameter D4. Probe 28 has a length l1.

Thread 32 has a substantially triangular thread form and is configured to penetrate bone. In some embodiments, thread 32 is configured for engagement and fixation with cortical bone, cancellous bone, include both cortical thread and cancellous thread portions, and/or a lag configuration, as described herein. In some embodiments, the thread form can be variously configured, such as, for example, V-shaped, buttress, isosceles, scalene, equilateral, truncated, square and/or trapezoidal. In some embodiments, thread 32 can be coarse, fine and/or configured for engagement with a selected portion of vertebral tissue, such as, for example, cortical and cancellous bone.

In some embodiments, other engaging structures may be located on probe 28, such as, for example, a nail configuration, barbs, expanding elements, raised elements and/or spikes to facilitate engagement of probe 28 with tissue, such as, for example, vertebrae.

The outer surface of probe 28 includes a thread surface comprising thread 32 and a substantially even surface 38. The thread surface comprising thread 32 includes a first axially threaded portion, such as, for example, surface 34 and a second axially threaded portion, such as, for example, surface 36 spaced apart from surface 34. First and second threaded surfaces 34, 36 extend in a linear configuration from portion 22, and directly from transition 48, to a distal tip 46. Surfaces 34, 36 have an arcuate outer circumference. In some embodiments, first and second surfaces 34, 36 are variously configured, such as, for example, those alternatives described herein.

Surface 38 includes a first axial portion, such as, for example, a substantially planar surface 40, and a second axial portion having a substantially planar surface (not shown), similar to surface 40, and spaced apart from surface 40. The planar surfaces extend from portion 22, and directly from transition 48, to distal tip 46. In one embodiment, the planar surfaces 40 are disposed between threaded surfaces 34, 36 in a substantially parallel orientation. Other embodiments may have more than two planar surfaces spaced radially evenly around the probe, or in some other arrangement including a helical configuration around the circumference of the probe. The planar surfaces and surfaces 34, 36 extend linearly and are disposed in a substantially side by side orientation along longitudinal axis LA The planar surfaces are separated from surfaces 34, 36 by boundaries B1, B2 respectively, which extend between transition 48 and distal tip 46, in a substantially parallel orientation along longitudinal axis L1. In some embodiments, all or only a portion of the surfaces of probe 28 can be alternatively oriented, similar to those alternatives described herein.

Probe 28 includes distal tip 46 at its distal most end 50, which is configured for penetrating bone tissue. Distal tip 46 of probe 28 is tapered towards distal most end 50. Radial cutting flutes 44 are disposed at distal tip 46. In some embodiments, distal tip may include alternate configurations, such as, for example, pointed tip, blunt tip and/or multiple points. The distal tip may be shaped to self-center the trajectory of the bone fastener within the softest bone in a pedicle after an outer cortex of the pedicle is punctured.

The radial cutting flutes 44 may be oriented opposite each other directionally. In such an embodiment, a first radial cutting flute 44 cuts bone when the bone fastener 10 is rotated clockwise, while a second cutting flute 44 cuts bone when the bone fastener 10 is rotated in a counter-clockwise direction. The bone fastener 10, then, may be advanced into bone by oscillating between a clockwise and counterclockwise rotation of the bone fastener 10 to advance the bone fastener 10 into the bone. First and second cutting flutes 44 may be oriented on a single planar surface 40, may be oriented on each of the planar surfaces in embodiments with multiple planar surfaces 40, or the first flute 44 may be oriented on a first surface 40 while the second flute 44 may be oriented on a different planar surface 40

Figure 3:
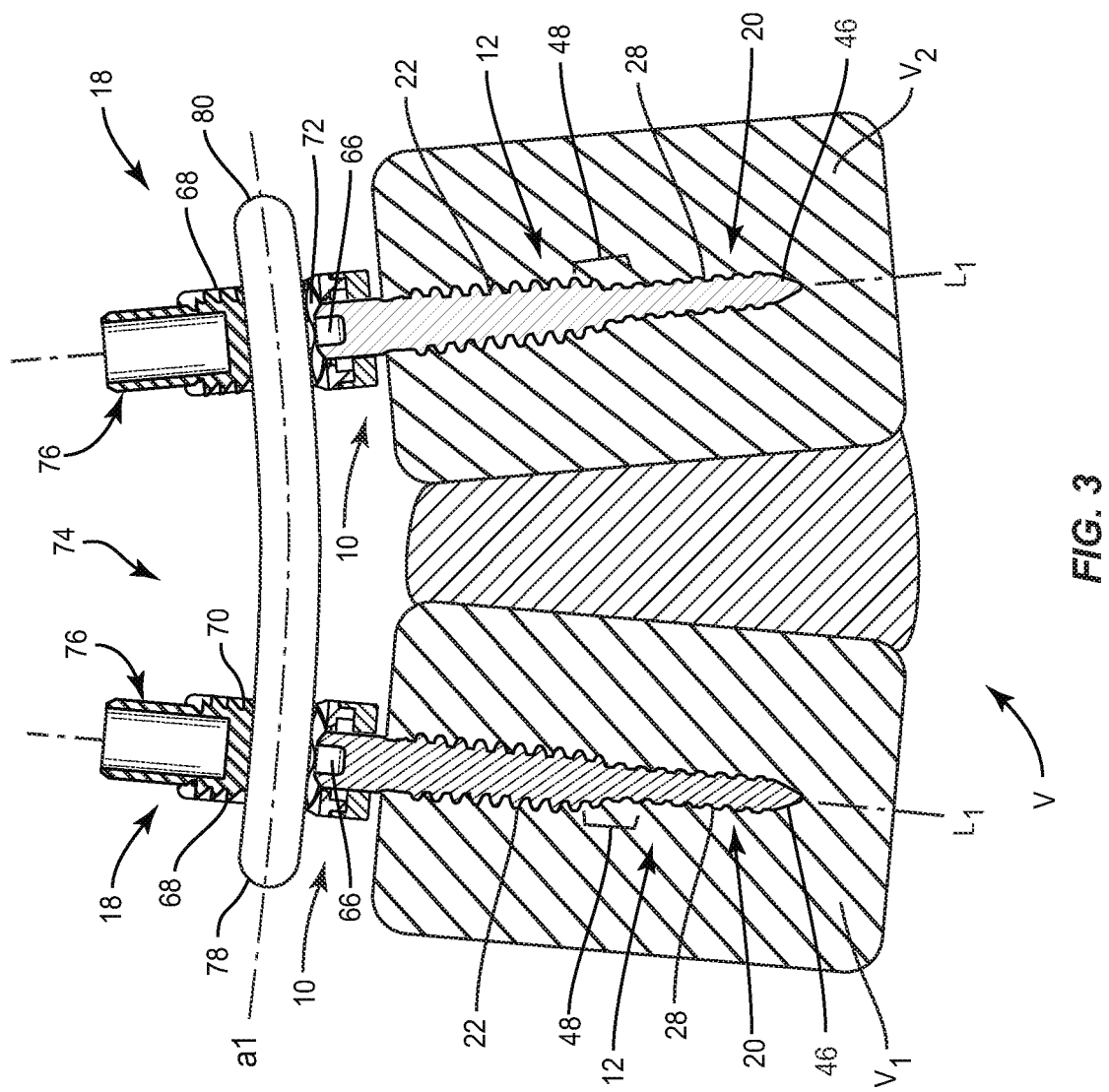
FIG. 3 is side view of a system in accordance with the principles of the present disclosure disposed with vertebrae.

In one embodiment, as shown in FIG. 3, first end 18 includes shaft 12 and spaced apart arms 68 having an inner surface 70 that defines an implant cavity 72. Implant cavity 72 defines an axis a1 transverse to longitudinal axis L1. Implant cavity 72 is configured to receive and movably support at least a portion of an implant, such as, for example, a vertebral rod 74. At least a portion of inner surface 70 is threaded and engageable with a coupling member, such as, for example, setscrew 76.

First end 18 of shaft 12 includes an inner surface that defines a socket cavity 66 configured for engagement with a tool or instrument for engaging and fastening bone fastener 10 with tissue and/or implants, such as, for example, plates and connectors. Cavity 66 receives a surface of a drive element of the tool that matingly engages the inner surface of end 18 for manipulating bone fastener 10. It is envisioned that the surfaces of cavity 66 and the drive element can be alternatively configured, such as, for example, thread form, triangular, square, polygonal, hexalobular, star, torx, Irregular, uniform, non-uniform, offset, staggered and/or tapered.

In assembly, operation and use, a spinal implant system including one or a plurality of bone fasteners 10, similar to that described above, is employed with a surgical procedure for treatment of a spinal disorder affecting a section of a spine of a patient, as discussed herein. In particular, the spinal implant system is employed with a surgical procedure for treatment of a condition or injury of an affected section of the spine including vertebrae V, as shown in FIG. 3. It is contemplated that bone fasteners 10 are attached to vertebrae V for a surgical arthrodesis procedure, such as fusion, and/or a dynamic stabilization application of the affected section of the spine to facilitate healing and therapeutic treatment.

In use, to treat the affected section of the spine, a medical practitioner obtains access to a surgical site including vertebra V in any appropriate manner, such as through incision and retraction of tissues. It is envisioned that the spinal implant system including bone fastener 10 may be used in any existing surgical method or technique including open surgery, mini-open surgery, minimally invasive surgery and percutaneous surgical implantation, whereby the vertebrae V is accessed through a micro-incision, or sleeve that provides a protected passageway to the area. Once access to the surgical site is obtained, the particular surgical procedure is performed for treating the spinal disorder. Bone fastener 10 is then employed to augment the surgical treatment. The components of the spinal implant system can be delivered or implanted as a pre-assembled device or can be assembled in situ. The spinal implant system may be completely or partially revised, removed or replaced.

An incision is made in the body of a patient and a cutting instrument (not shown) creates a surgical pathway for implantation of components of the spinal implant system. A preparation instrument (not shown) can be employed to prepare tissue surfaces of vertebrae V, as well as for aspiration and irrigation of a surgical region according to the requirements of a particular surgical application.

A surgical site is identified for implantation of bone fasteners 10 with vertebrae V1, V2 respectively. Bone fasteners 10 are delivered along the surgical pathway to the surgical site adjacent vertebrae V1, V2 for penetrating engagement with vertebral tissue. Each bone fastener 10 is oriented such that tip 46 is engaged within vertebral tissue, such as, for example, the cortical wall of each of vertebrae V1, V2. Probe 28 is manipulated to penetrate and pass through the cortical wall for starting and/or tapping a cavity in vertebrae V1, V2 to enable threading of bone fasteners 10 with vertebrae V1, V2. The shallow probe configuration of the surfaces probe 28, described above, facilitate passage through the vertebral tissue. The probe may be used to probe an inner wall of the pedicle to verify no external violation of an external wall of a pedicle has occurred. The probing step may also occur as the surgeon is oscillating the probe through the pedicle. A surgeon may begin the step of advancing the probe into the pedicle, but may pull the probe out and probe the walls before completing the trajectory through the pedicle. Before the probe has advanced too deep into the pedicle (around, in most cases, 10 mm) the trajectory of the bone fastener may be changed if the surgeon determines the cortical wall of the pedicle has been violated during the initial advancement of the bone fastener.

A drive element of a tool is engaged with cavity 66 to manipulate bone fastener 10. With surfaces 34, 36 disposed with cancellous and/or cortical tissue of vertebrae V1, V2, bone fastener 10 is advanced by rotating and/or oscillating the bone fastener 10 such that probe 28 is inserted into vertebral tissue of vertebrae V1, V2 and additional vertebrae as dictated by the procedure. Once bone fastener 10 is inserted into tissue up to transition 48, continued threading rotation allows axial translation of bone fastener 10 into tissue threads portion 22 into the cancellous and/or cortical tissue of vertebrae V1, V2. Each bone fastener 10 is inserted or otherwise engaged with vertebrae V1, V2, according to the particular requirements of the surgical treatment, to fix each bone fastener 10 with vertebrae V1, V2, respectively. The drive element may be power assisted. The power assisted drive element may provide an added advantage when inserting a bone fastener 10 as described herein. The power assist may provide appropriate amounts of torque to the bone fastener 10 to facilitate the implantation of the bone screw in a single step.

Bone fasteners 10 are configured and selectively oriented to attach upper section 78 of vertebral rod 74 to vertebra V1 and lower section 80 of vertebral rod 74 to adjacent vertebra V2. Setscrews 76 are torqued and threaded with spaced apart arms 68 to securely attach rods 74 with vertebrae V1, V2. In this configuration, vertebral rod 74 is securely disposed within implant cavity 72 and bone fasteners 10 are fixed to vertebrae V1, V2.

It is contemplated that the spinal implant system can include one or a plurality of bone fasteners such as those described herein and/or fixation elements, which may be employed with a single vertebral level. It is further contemplated that the bone fasteners may be engaged with vertebrae in various orientations, such as, for example, series, parallel, offset, staggered and/or alternate vertebral levels. It is envisioned that the bone fasteners and/or fixation elements may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, the spinal implant system includes an agent, which may be disposed, packed or layered within, on or about the components and/or surfaces of the spinal implant system. In some embodiments, the agent may include bone growth promoting material, such as, for example, bone graft to enhance fixation of the bone fasteners with vertebrae V. In some embodiments, the agent may include one or a plurality of therapeutic agents and/or pharmacological agents for release, including sustained release, to treat, for example, pain, inflammation and degeneration.

The components of the spinal implant system can be made of radiolucent materials such as polymers. Radiomarkers may be included for identification under x-ray, fluoroscopy, CT or other imaging techniques. In some embodiments, the use of microsurgical and image guided technologies may be employed to access, view and repair spinal deterioration or damage, with the aid of the spinal implant system. Upon completion of the procedure, the surgical instruments, assemblies and non-implant components of the spinal implant system are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for inserting a bone fastener, comprising the steps of:
   puncturing bone with a distal tip of the bone fastener;
   oscillating the bone fastener clockwise and counter-clockwise to axially advance the bone fastener to a first depth; and
   rotating the bone fastener after the bone fastener has reached the first depth to threadingly engage bone and advance the bone fastener to a second depth,
   wherein the bone fastener oscillates clockwise and counter-clockwise as the bone fastener advances axially to the first depth.

2. The method of claim 1, wherein the oscillating step comprises cutting bone with a first cutting flute when the bone fastener is oscillated in a first of the clockwise or counter-clockwise direction.

3. The method of claim 2, wherein the oscillating step further comprises cutting bone with a second cutting flute when the bone fastener is oscillated in a second of the clockwise or counter-clockwise direction.

4. The method of claim 3, wherein:
   the bone fastener comprises a shaft comprising a thread, the thread being interrupted by a planar surface;
   the first and second cutting flutes are each positioned on the planar surface.

5. The method of claim 3, wherein:
   the bone fastener comprises a shaft comprising a thread, the thread being interrupted by a first planar surface and a second planar surface that is spaced apart from the first planar surface; and
   the first cutting flute is positioned on the first planar surface and the second cutting flute is positioned on the second planar surface.

6. The method of claim 1, further comprising the step of probing an inner wall of the pedicle to verify no external violation of an external wall of a pedicle has occurred.

7. The method of claim 6, wherein the probing step occurs during the oscillating step.

8. The method of claim 1, wherein the bone fastener comprises:
   a first end; and
   a second end defining a longitudinal axis, the second end having a first portion having a thread diameter and a core diameter, and a second portion having a core diameter less than the core diameter of the first portion, the second portion including the distal tip, a threaded surface and a substantially flat surface.

9. The method of claim 8, wherein the threaded surface includes a first axial portion and a second axial portion spaced apart from the first axial portion.

10. The method of claim 8, wherein the flat surface includes a first axial portion and a second axial portion spaced apart from the first axial portion.

11. The method of claim 10, wherein the first cutting flute is adjacent the first axial portion, the first cutting flute configured to cut the bone when the bone fastener is rotated in a first of the clockwise and counterclockwise direction, the bone fastener further comprising a second cutting flute configured to cut bone when the bone fastener is rotated in a second of the clockwise and counterclockwise direction.

12. The method of claim 11, wherein the second cutting flute is adjacent the second axial portion.

13. The method of claim 11, wherein the second cutting flute is adjacent the first axial portion.

14. The method of claim 8, wherein the bone fastener comprises a transition disposed between the first portion and the second portion, the transition being disposed at an angular orientation in a range of approximately 10 through 30 degrees relative to the axis.

15. The method of claim 8, wherein the second portion is monolithically formed with the first portion.

16. A method for inserting a bone fastener, comprising the steps of:
   puncturing bone with a distal tip of the bone fastener such that the distal tip is disposed at a first depth within the bone;
   rotating the bone fastener clockwise to advance the bone fastener distally such that the distal tip is disposed at a second depth within the bone that is greater than the first depth;
   rotating the bone fastener counter-clockwise to advance the bone fastener distally such that the distal tip is disposed at a third depth within the bone that is greater than the second depth; and
   rotating the bone fastener after the bone fastener has reached the third depth to threadingly engage bone and advance the bone fastener to a fourth depth.

17. The method of claim 16, wherein the bone fastener is rotated clockwise to advance the bone fastener to the fourth depth, the fourth depth being greater than the third depth, and the method further comprises rotating the bone fastener counter-clockwise to advance the bone fastener distally such that the distal tip is disposed at a fifth depth within the bone that is greater than the fourth depth.

18. The method of claim 16, wherein the bone fastener is rotated clockwise to the fourth depth after the bone fastener is rotated counter-clockwise to the third depth and the bone fastener is rotated counter-clockwise to the fifth depth after the bone fastener is rotated clockwise to the fourth depth.

19. A method for inserting a bone fastener, comprising the steps of:
   puncturing bone with a distal tip of the bone fastener;
   oscillating the bone fastener clockwise and counter-clockwise relative to the bone such that the each of the oscillations advance the bone fastener distally within the bone, wherein the bone fastener is oscillated until the distal tip is at a first depth within the bone; and
   rotating the bone fastener after the distal tip has reached the first depth to threadingly engage bone and advance the bone fastener to a second depth within the bone.

20. The method of claim 19, wherein the oscillating step comprises:
   cutting bone with a first cutting flute when the bone fastener is oscillated in a first of the clockwise or counter-clockwise direction; and
   cutting bone with a second cutting flute when the bone fastener is oscillated in a second of the clockwise or counter-clockwise direction.

* * * * *